(12) United States Patent
Kozlouski

(10) Patent No.: US 12,257,431 B2
(45) Date of Patent: Mar. 25, 2025

(54) BIPYRAMIDAL THERAPEUTIC DEVICE

(71) Applicant: Aleksandr Vasilievich Kozlouski, Smolyantsy (BY)

(72) Inventor: Aleksandr Vasilievich Kozlouski, Smolyantsy (BY)

( * ) Notice: Subject to any disclaimer, the term of this patent is extended or adjusted under 35 U.S.C. 154(b) by 1174 days.

(21) Appl. No.: 16/873,539

(22) PCT Filed: Oct. 23, 2018

(86) PCT No.: PCT/BY2018/000018
§ 371 (c)(1),
(2) Date: Apr. 9, 2021

(87) PCT Pub. No.: WO2019/084652
PCT Pub. Date: May 9, 2019

(65) Prior Publication Data
US 2021/0228894 A1 Jul. 29, 2021

(51) Int. Cl.
*A61N 1/16* (2006.01)
*A61M 21/00* (2006.01)
(Continued)

(52) U.S. Cl.
CPC .............. *A61N 1/16* (2013.01); *G01N 27/10* (2013.01); *A61M 2021/0027* (2013.01); *A61M 2021/005* (2013.01); *A61M 2205/0288* (2013.01)

(58) Field of Classification Search
CPC ............ A61N 1/16; A61N 5/00; G01N 27/10; A61M 2021/0027; A61M 2021/005; A61M 2205/0288; C02F 1/005
See application file for complete search history.

(56) References Cited

FOREIGN PATENT DOCUMENTS

| RU | 2109527 C1 | * | 4/1998 |
| RU | 2184574 C2 | * | 7/2002 |
| RU | 2259188 C1 | * | 8/2005 |

* cited by examiner

*Primary Examiner* — Carrie R Dorna
*Assistant Examiner* — Joshua Daryl D Lannu
(74) *Attorney, Agent, or Firm* — Michael D. Eisenberg

(57) ABSTRACT

The invention relates to medical equipment and can be used to prevent human exposure to sources of negative energy in geopathic zones and to electromagnetic radiation.

The device comprises two pyramids 1, 2 in the form of hollow vessels sharing a common apex 4 and interconnected by a tubular channel 11. A base 8 of an upper pyramid 2 is provided with a removable lid 9. An antenna represents an EH-antenna 3 having oscillators in the form of the pyramids 1, 2, the parameters of which are consistent with the golden section, satisfy an even number from the Fibonacci series (F2=1.62), and are specified by the formula: $\alpha=2h^2/s$, where a is the side length of the bases, h is the height of each pyramid, and s is the apothem. A toroidal permanent magnet 14 is assembled on the outer surface of the tubular channel 11, and an audio/video device 19 along with a means for monitoring the physical parameters of the liquid medium within the volume of the pyramids 1 and 2 are mounted in the leak-proof compartment of cavity 13 of the lower pyramid 1. Lid 9 of base 8 of the upper pyramid 2 has a photovoltaic power source 10 disposed thereon for providing operation of the audio/video device 19 and means 18 for monitoring the physical parameters of the liquid medium within the volume of the pyramids 1 and 2.

6 Claims, 2 Drawing Sheets

(51) Int. Cl.
    *A61N 5/00*     (2006.01)
    *C02F 1/00*     (2023.01)
    *G01N 27/10*     (2006.01)

BIPYRAMIDAL THERAPEUTIC DEVICE

The invention relates to medical equipment and can be used to carry out therapeutic procedures in order to prevent the consequences of human exposure to harmful electromagnetic radiation and to reduce the effect of negative energy sources of geopathic zones.

A prolonged stay of a person in a geopathic zone is known to cause discomfort, weakness, drowsiness or insomnia, headaches, as well as a number of other functional disorders of the human body [1]. Geopathic zones (GZ) have both natural and artificial origin. It has been established that they have an energy-field nature, and their formation is due to the manifestation of electromagnetic fields of various origins.

To suppress or neutralize the GZ radiation, various technical means, as well as prevention methods with respect to a body exposed to the harmful negative energy of these zones, have been proposed. Numerous studies have established that effective protection from the harmful GZ radiation can be provided by pyramid-shaped structures, which also favorably influence biological objects as a result of the shape effect by causing a spontaneous change in the physicochemical or biological structure of the object located inside such structure [2]. It was found that a semi-spherical energy field is formed at the base of the pyramid characterized by a concentration of the pathogenic fields of the natural Earth's energy grids (e.g., Hartmann grid, Curry grid, etc.), while the surrounding energy is accumulated through the faces of the pyramid and released from the point of common apex of the pyramid faces [3]. The research conducted by Professor A. I. Veinik has shown that the energy-field nature of the GZ radiation is a variety of chronal radiation capable of changing the density of the matter as a result of chrononchronous interaction between atoms and molecules of the irradiated matter. Such processes are described by an equation, which includes time, which justifies a possible existence of thermodynamic pairs with a chronal matter circulating therewithin, or a difference in chronals, without which none of the living organisms could survive, will be a driving force of circulation of some other matter [4].

For example, an autonomous relaxation phyto-sauna "Pyramid" is known, which utilizes the shape effect [5]. The therapeutic properties of a phyto-sauna pyramid support the above studies performed by Professor A. I. Veinik concerning the positive effect of chronal radiation on the body as a result of optimization of the chronal matter circulation within the pyramidal shape. Such phyto-sauna contains a prism-shaped wood cabin with a door, a phyto-tank with a leak-proof lid filled with aqueous infusion of medicinal herbs, which is placed over a heating element and connected with the cabin via a tube or a hose through the holes made in the phyto-tank lid. The lower part of the cabin has the shape of a triangular prism or a pyramid with leak-proof window, and is provided with an inclined bottom having grooves to drain condensate and a tray for collecting it. The cabin is equipped with a seat with armrests and a back made of narrow wooden slats installed with some spacing, and provided with a regulator to control the horizontal position of the back and reflective screens in the form of shields mounted on a stand. The reflective screens are made of wood and configured to move around the patient and allow changing the shield position in different planes. A thermometer is also provided, and the tube or hose at the cabin inlet is divided into two parts. The height of the cabin provides for some free airspace above the patient's head. The trihedral shape of the cabin causes a relaxing effect on the nervous system and promotes normal functioning of the energy channels of the human body, which help restore normal functioning of the internal organs.

A disadvantage of the known pyramid design include limited possibilities in terms of neutralizing the GZ radiation, which is caused by the structural design of the pyramid embodied exclusively as a bathing complex.

In patent [6], it is proposed to use for treatment pyramids having various bases (trihedral, tetrahedral, polygonal, combined) and structures (full, truncated, hollow, monolithic, frame), made of various materials of natural or artificial origin. The pyramid is installed and oriented in space along the cardinal directions. It has been found that the energy concentration distribution zones within the pyramid and beyond are defined according to the following sequence: first zone inside the pyramid from its apices is equal to 0.2360680H, second zone—0.263932H, third zone—0.309014H, and fourth zone—0.190983H, where H is the height of the pyramid. Beyond the pyramid, the fifth zone in located under the pyramid along its entire height; the sixth zone-sideways from its northern edge; the seventh zone-above the pyramid; the eighth zone-sideways from the southern edge of the pyramid; the ninth zone-sideways from the eastern edge of the pyramid, and the tenth zone-sideways from the western edge of the pyramid. The energy concentration is higher closer to the pyramid. As the distance from the pyramid increases, the energy level of the zones located beyond the pyramid becomes lower.

The disadvantage of such type of pyramids includes the inability to control the distribution of energy along the pyramid zones, which depends exclusively on the spatial orientation of the pyramid relative to the cardinal directions.

A device for neutralizing harmful radiations according to patent [7] was chosen as a prototype. The device is intended for use primarily indoors and, depending on the capacity, can be used to protect a workplace, apartment, cottage, or a building. The device comprises an accumulator in the form of a regular pyramid spatially oriented relative to the cardinal directions. The pyramid further contains an emitter, an antenna, and an additional accumulator in the form of a pyramid. The accumulator pyramids share a common apex and are arranged symmetrically to each other relative thereto. The antenna passes through a common apex and is parallel to the bases of the pyramids, while the emitter is tied to the common apex. The accumulator pyramids have a frame structure with triangular base. The antenna is embodied in the form of a horizontal arm and is provided with receivers placed at the ends of said horizontal arm using oppositely oriented vertical arms. The emitter is embodied in the form of a sphere made of finely dispersed materials held together by a binding mass, wherein the center of said sphere is tied to the common apex of the pyramids. The emitter can also be made in the form of two truncated cones, each facing the common apex of the pyramids with their smaller bases and positioned coaxially inside the internal cavity of the respective pyramid. Such truncated cones and made of finely dispersed materials held together by a binding mass, and are located symmetrically to each other relative to the common apex of the pyramids. The emitter contains two waveguides in the form of metal funnels with accelerators positioned coaxially with the pyramids. Furthermore, the accelerators are embodied in the form of spirals arranged inside the funnels coaxially thereto. The finely dispersed materials include ceramic, metallic, and organic powders treated with electromagnetic radiation. One of the edges of the accumulator pyramids, the horizontal projection of which is located at a certain angle relative to the horizontal projection of the antenna, represents a dedicated edge, relative to which the device is oriented in space.

Depending on the arrangement, the device condition is either "ON" or "OFF". In the "ON" condition, the device is installed vertically at a lower point (on the floor, lower level, or basement) of the building with the dedicated edge facing either north or south. In all other positions, including horizontal, the device is in "OFF" condition. The installation location of the device inside the building is selected depending on its capacity. The optimal location is the geometric center of the building. The device capacity depends on its geometrical dimensions and is characterized by a radius of the coverage area, which determines the area of the circle within which it performs effectively. Due to their pyramidal shape, the accumulators first accumulate and then emit into the ambient the Orgone energy, which neutralizes the electromagnetic radiation of various origins causing harmful effects on humans.

The disadvantage of the prototype includes structural design of the antenna, representing a separate component of the device, and the presence of the emitter with an accelerator to ensure effective performance of the device, which complicate the fabrication thereof.

The objective of the invention is to eliminate the indicated structural disadvantages of the prototype and expand the functionality of the device.

The technical result of the invention consists of reducing the loss resistance in the antenna operating range and improving the efficiency of the pyramidal device for suppressing and neutralizing electromagnetic radiation of various origins and, thereby, increasing the therapeutic efficacy.

The technical result is achieved by the fact that in the proposed bipyramidal therapeutic device, comprising two regular pyramids sharing a common apex, positioned symmetrically to each other relative to the apices, and spatially oriented according to the cardinal directions, and an antenna, according to the invention, said pyramids are embodied in the form of the vessels having internal cavities, wherein the base of the upper pyramid contains a removable lid, while the antenna represents an EH-antenna having oscillators in the form of pyramids, the parameters of which are consistent with the golden section, satisfy an even number from the Fibonacci series (F2=1.62), and are specified by the formula: $\alpha=2h^2/s$, where a is the side length of the bases, h is the height of each pyramid, and s is the apothem; furthermore, the common apex is provided with a through channel interconnecting the cavities of the pyramids, while the outer surface of the channel bears a toroidal permanent magnet assembled thereon, the magnetic induction vector of which is oriented toward the lower base of the pyramid, while the cavity of the lower pyramid houses an audio-video device and a means for monitoring the physical parameters of the liquid medium within the pyramid volume, and the lid of the base of the upper pyramid bears a photovoltaic power source to support operation of the audio-video device and the means for monitoring the physical parameters of the liquid medium within the pyramid volume.

The channel interconnecting the pyramid cavities is provided with interchangeable inserts to adjust its flow area.

The EH-antenna is characterized by a loss resistance in the HF range of 0.45-0.48 Ohm and efficiency of 0.018-0.02 dB.

The means for monitoring the physical parameters of the liquid medium is embodied in the form of an instrument for measuring specific electrical conductivity of water.

The cavity of the lower pyramid is provided with a leak-proof partition dividing it height-wise at a 1:3 ratio and forming a compartment in the lower part of the pyramid for installing the audio-video device and the means for monitoring the physical parameters of the liquid medium.

The cellular-honeycomb structure of the lining material has a porosity of 0.75-0.92.

The substance of the invention is illustrated by drawings shown in FIGS. 1-4.

Figures 1, 2:
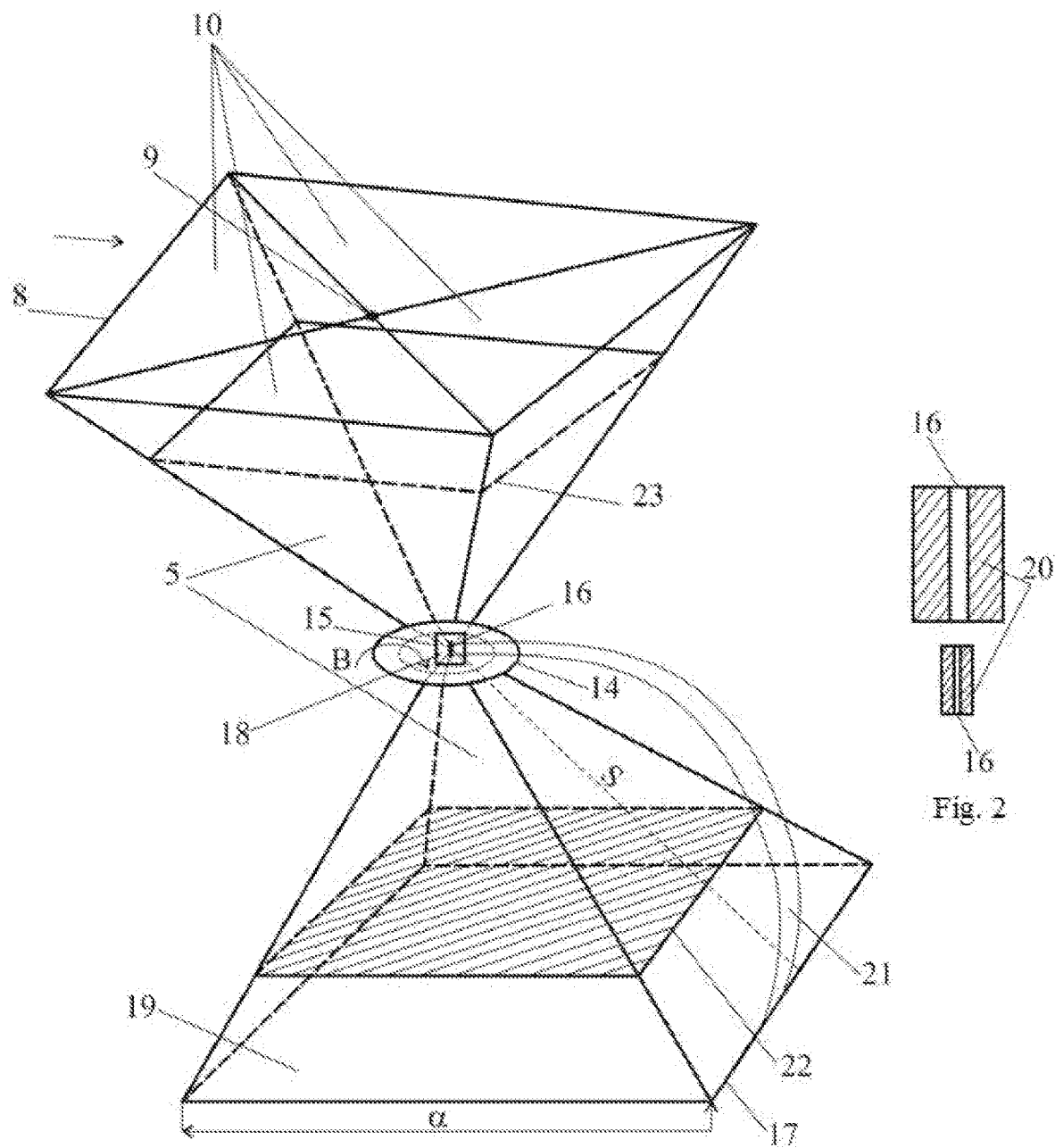
FIG. 1 shows a schematic diagram of the bipyramidal device.
FIG. 2 shows a longitudinal cross-sectional view of the insert at the common apex of the pyramids.

The device comprises two regular tetrahedral pyramids 1 and 2 with triangular faces-walls 5 and a common apex 4, and forming an EH-antenna 3 with oscillators in the form of said pyramids 1 and 2, representing vessels with cavities 12, 13; the side faces-walls 5 are covered with lining material 6 having a cellular-honeycomb structure 7; a base 8 of the upper pyramid 2 represents a removable lid 9 with a photovoltaic power source 10 mounted thereon; the common apex 4 is provided with a tubular channel 11 interconnecting cavities 12, 13; a toroidal permanent magnet 14 mounted on the outer surface 15 of the tubular channel 11; a means 18 for monitoring the physical parameters of the liquid medium and an audio-video device 19 installed within cavity 13 of the lower pyramid 1 in the compartment separated by a leak-proof partition 22; and interchangeable inserts 20 for adjusting flow section 16 of the tubular channel 11.

The bipyramidal therapeutic device is assembled as follows.

Figures 3, 4:
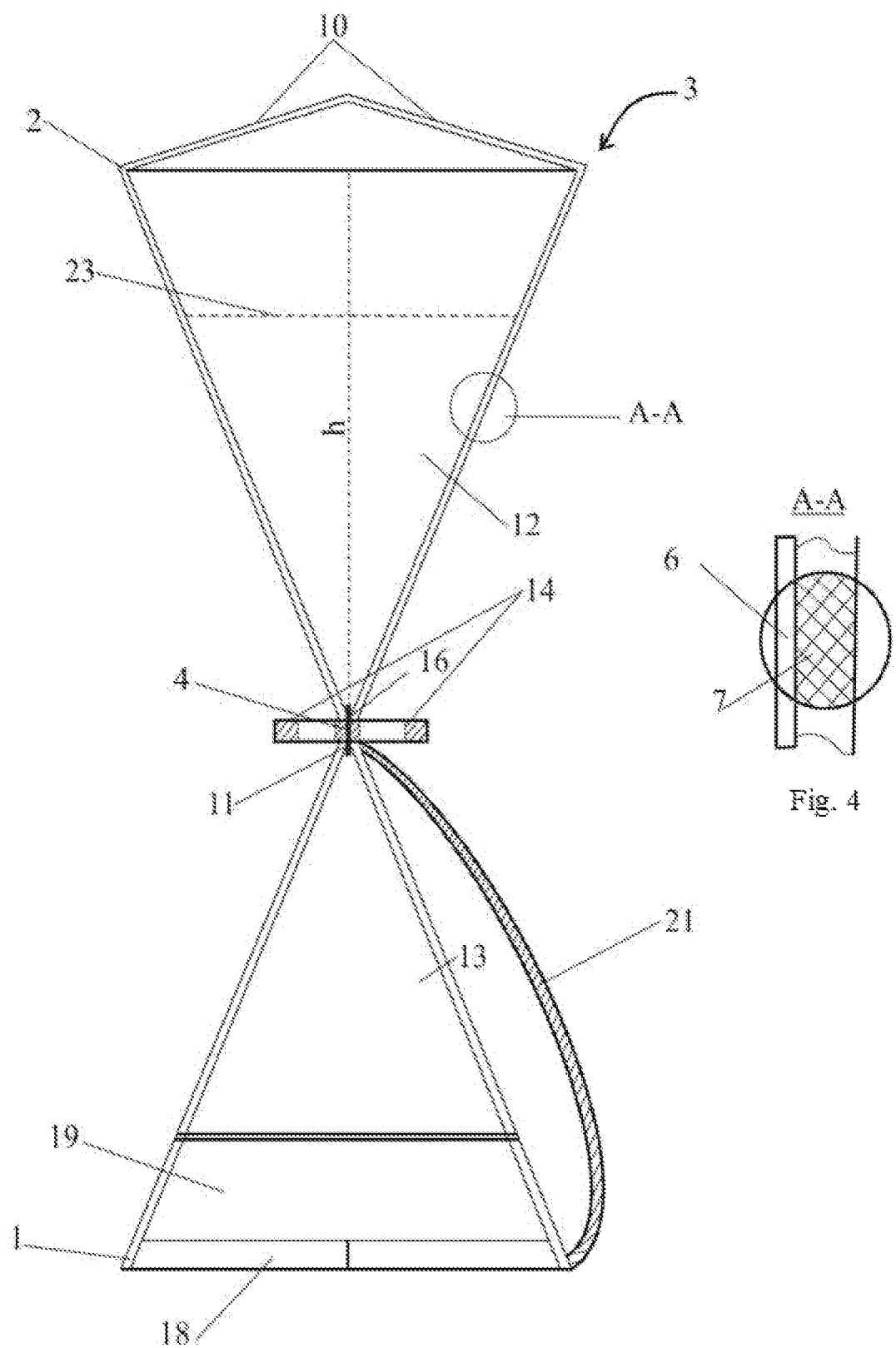
FIG. 3 shows a longitudinal cross-sectional view of the device.
FIG. 4 shows a fragment of the wall lining of the pyramid (view A-A).

Pyramids 1 and 2 are fabricated with bases 17 and 8 in the form of rectangular quadrangles. As will be obvious for those skilled in the art, pyramids 1 and 2 may also have a different number of faces, such as six, eight or more. Pyramids 1, 2 have frame structure and are made in the form of the vessels with cavities 12, 13 limited by side triangular faces-walls 5. The edges of the framework of pyramids 1, 2 and faces-walls 5 are made of copper, brass or other electrically conductive material, while the outer surface of faces-walls 5 are covered with lining material 6 having a cellular-honeycomb structure 7 (see view A-A in FIG. 4), characterized by a porosity of 0.75-0.92. Lining material 6 may include foamed metals, such as bronze, aluminum, or non-metallic materials, such as paper, cardboard, etc., which are pretreated to form a specified structure 7 with cellular-honeycomb configuration. The characteristic pore sizes are chosen in a way to ensure the optimal energy interaction of the lining material 6 with the ambient environment in order to neutralize pathogenic electromagnetic radiation of various origins and increase the therapeutic effect.

Next, pyramids 1 and 2 are used to assemble EH-antenna 3. To do this, said pyramids are connected to each other by their apices, which are precut to obtain flat areas (not shown in the drawing) to enable their connection with the formation of a common apex 4, while cavities 12, 13 are connected by a tubular channel 11 made of electrically conductive material (copper, bronze, brass, etc.). To adjust the diameter of the flow section 16 of the tubular channel 11, replaceable inserts 20 are used, which control the flow rate of the liquid medium (e.g., boiled water or solutions thereof) passing from cavity 12 of the upper pyramid 2 to cavity 13 of the lower pyramid 1 under the effect of gravity.

The parameters of pyramids 1, 2 and, thus, the dimensions of the oscillators of EH-antenna 3, are selected to be consistent with the golden section and satisfy an even number from the Fibonacci series (F2=1.62), calculated using the following formula: $\alpha=2h^2/s$, where $\alpha$ is the side length of the pyramid bases, h is the height of each pyramid, and s is the apothem. Furthermore, along with other electronic components (not shown in the drawing) of EH-antenna 3, the loss resistance in the HF range of 0.45-0.48 Ohm and the efficiency thereof ranging from 0.018 to 0.02 dB were ensured.

A toroidal permanent magnet 14 is mounted on the outer surface 15 of the tubular channel 11. Furthermore, to achieve a desired effect of the magnetic field on the treated liquid medium (boiled water or solutions thereof, including alcohol-containing), the magnetic induction vector is oriented toward the base 17 of the lower pyramid when passing liquid from the upper pyramid 2 to the lower pyramid 1. The magnet is chosen to have a magnetic induction in the range between 100 and 200 mT (1000-2000 Gauss), which ensures effective magnetization of the liquid medium as it passes from the upper pyramid 2 cavity to the lower pyramid 1 cavity.

Installed on base 17 inside cavity 13 of the lower pyramid 1 are a battery (not shown in the drawing), means 18 for monitoring the physical parameters of the liquid media, and audio-video device 19 equipped with a read-out laser head, all connected to the photovoltaic power source 10 to ensure operation thereof, as well as to recharge the battery. Furthermore, a leak-proof partition 22 is mounted inside the cavity of the pyramid 1 at a height of ⅓ to separate the upper ⅔ of the volume of cavity 13 from the compartment in the lower part of this cavity intended for the audio-video device 19 and means 18 for monitoring the physical parameters of the liquid medium.

The device operates as follows.

In preparation for operation, the bipyramidal device is installed vertically relative to the ground surface and spatially oriented according to the cardinal directions using a leveling instrument and a compass (not shown in the drawing). To do this, one of the faces-walls 5 of the pyramids 1 and 2 is oriented using a compass (not shown in the drawing) along the north-south direction. Means 18 for monitoring the physical parameters of the liquid medium and audio-video device 19 are connected to photovoltaic power source 10 to ensure their operation. Next, cavity 12 of the upper pyramid 2 is filled with the treated medium (e.g., boiled drinking water) to a level 23 corresponding to ⅔ of the volume of cavity 12, where the most effective zone for accumulating positive Orgone energy of the pyramidal device is located. Next, tubular channel 11 is opened and water is directed to cavity 13 of the lower pyramid 1, where it continues to be treated with positive Orgone energy in a similar zone, which also constitutes ⅔ of the total volume of the lower pyramid 1 separated by leak-proof partition 22. To ensure effective magnetization of water, its flow rate through channel 11 is controlled by adjusting the cross-section of the channel using interchangeable inserts 20. As water flows down through channel 11, it undergoes magnetization by toroidal permanent magnet 14 with magnetic induction B=100-200 mT, which enables restructuring thereof and removal of magnesium and calcium salts. Concurrently, while flowing down through channel 11, water is treated acoustically by supplying an audio signal from the audio-video device 19 through an external acoustic channel 21. This is done by playing musical tunes at frequencies favorably affecting the human body.

Water treatment is controlled by measuring specific electrical resistance using means 18 for monitoring the physical parameters of the liquid media. An AP-2 device of the AquqPro line can be used as an example of monitoring means 18 to measure electrical conductivity of water [9].

An increased efficiency of accumulating positive Orgone energy by the pyramidal device within zones corresponding to ⅔ of the total volume of the pyramids 1 and 2 is provided by selecting the values of parameters $\alpha$ (side length of the bases 17 and 8), h (height), and s (apothem) of the pyramids 1, 2, which correspond to the golden section with an even Fibonacci number F2=1.62. Since pyramids 1 and 2 also serve as oscillators of EH-antenna 3, and the selected values of parameters $\alpha$, h, and s of the pyramids 1 and 2 provide the EH-antenna in the HF range with low loss resistance (0.45-0.48 Ohms with efficiency of 0.018-0.02 dB), EH-antenna 3 with a height of one pyramid (h=15 cm) effectively emits electromagnetic oscillations modulated by the emission of Orgone energy of the pyramids, and neutralizes harmful emissions of man-made and natural origin in the surrounding space. In addition, water contained in cavities 12 and 13 of the pyramids 1, 2 is also subjected to treatment with positive Orgone energy and undergoes structural changes.

With a total height of the bipyramidal device (BPD) of about 30 cm, its operating range can be estimated using the following formula: $R=10^4 \cdot r/2$, where r is the total height of the pyramids 1, 2 equal to 2h. If r=0.3 m, the BPD effect extends over a distance of about 1500 m.

The effect of neutralization of harmful radiation can also be enhanced by lining the outer surfaces of faces-walls 5 of the pyramids 1, 2 with material 6 having a cellular-honeycomb structure 7 with porosity of 0.75-0.92. Examples of lining material 6 include foam metals, such as bronze, aluminum, or non-metallic materials, such as paper, cardboard, etc., which are pre-processed to obtain specified structure 7 with cellular-honeycomb configuration and porosity. The cellular sizes are selected in a way to ensure the maximum energy interaction of the lining 6 with the ambient environment and to enhance the therapeutic effect on the human body.

The high efficiency of water treatment using the pyramidal device is also caused by the turbulence processes in the water jet as it passes through channel 11, which is associated with the effect of self-organization of the vortex formation in the resonant flow regime of structured liquids, such as water after magnetic treatment. Such effect of self-organization of the vortex formation is a result of the fundamental mathematical law discovered by the French researcher Jean-Claude Perez [8], who studied the processes of self-organization of water-based structures similar to DNA molecules, the individual structural elements of which are naturally constructed according to the golden section rule.

After being treated in the bipyramidal device according to the invention, resultant water demonstrates a stimulating effect on the living organisms, as well as therapeutic properties caused by its structural features, the presence of which is evidenced by the steady changes in specific conductivity of such water.

The results of measuring specific electrical conductivity of different types of treated water using the monitoring means 18 are shown in Table 1.

| Types of water samples | Specific electrical conductivity, μS/m | Reactance, pF |
| --- | --- | --- |
| Tap drinking water | 36.20 | 345 |
| Distilled water | 0.63 | 0.36 |
| Drinking bottled water | 20.70 | 154 |
| Drinking frozen-out water | 18.90 | 167 |
| Tap frozen-out water | 22.40 | 149 |

Testing of the proposed bipyramidal therapeutic device under actual use conditions has shown that EH-antenna 3 is characterized in the HF range by a loss resistance of 0.41-0.51 Ohm at efficiency of 0.017-0.023, which falls within the specified range of characteristics and provides the technical result of the invention. In comparison with the prototype, the invention provides an increased radiation power, as well as more effective suppression and neutralization of harmful electromagnetic radiations due to the possibility of generating directional radiation enabled by the structural design of the EH-antenna, which, in essence, represents a miniature antenna version derived from the Hertz dipole, the radiation resistance of which approaches zero: $R_{rad}=X_c*\Delta f/f0$, where $X_c \geq 2000$ Ohm is the reactance.

SOURCES OF INFORMATION

1. V. E. Slavnikov, "Bipyramid," *Parapsikhologiya i psikhofizika*, No. 1, pp. 119-125 (1998).
2. SU 1803511 A1, Mar. 23, 1993, Bull. 11.
3. I. Yefimova, "Uncovered secrets of the pyramids," *Nauka i Religiya*, No. 4 (1997).
4. A. I. Veinik, "Thermodynamics of real processes," Navuka i Tekhnika, pp. 139-141, 382 (1991).
5. RU 2259188 C1, Aug. 27, 2005.
6. RU 2184574 C2, Jul. 10, 2002.
7. RU 2109527 C1, Apr. 27, 1998 (prototype).
8. A. P. Stakhov, "Sacred geometry and mathematics of harmony," site "Akademiya Trinitarizma," http://trinitas.ru/rus/djc/0202/010a/02020028.htm.
9. Analyzers of water quality. Instructions for use, Kiev, Jun. 6, 2017. Supplier: EcoUnit Ltd., www.ecoumt.com.ua.

What is claimed is:

1. A bipyramidal therapeutic device, comprising an upper pyramid (2) and a lower pyramid (1) sharing a common apex (4), positioned symmetrically with respect to each other and spatially oriented according to cardinal directions, and an antenna, wherein the upper pyramid (2) and the lower pyramid are embodied in the form of vessels having internal cavities (12, 13), where a base (8) of the upper pyramid (2) contains a removable lid (9), while the antenna is formed as an EH-antenna (3) having oscillators in the form of the upper pyramid (2) and the lower pyramid (1), parameters of which are consistent with a golden section, satisfy an even number from the Fibonacci series, wherein the even number from the Fibonacci series comprises F2, wherein F2=1.62, and are specified by the formula: $\alpha=2h^2/s$, where a is a side length of the base, h is the height of each pyramid, and s is an apothem; furthermore the common apex (4) is provided with a through channel (11) interconnecting the cavities (12, 13) of the lower pyramid (1) and the upper pyramid (2), while an outer surface of the channel (11) bears a toroidal permanent magnet (14) assembled thereon, a magnetic field induction vector of which is oriented toward a lower base (17) of the lower pyramid (1), while the cavity (13) of the lower pyramid (1) houses an audio-video device (19), and the lid (9) of the base (8) of the upper pyramid (2) bears a photovoltaic power source (10) to support operation of the audio-video device (19) and a means (18) for monitoring the physical parameters of a liquid medium in the volume of the lower pyramid (1) and the upper pyramid (2).

2. The bipyramidal device according to claim 1, wherein the channel (11) interconnecting the cavities (12, 13) of the pyramids (1, 2) is provided with interchangeable inserts (20) to adjust a flow area (16) thereof.

3. The bipyramidal device according to claim 1, wherein the EH-antenna (3) is characterized by a loss resistance in a range of 0.45 to 0.48 Ohm and efficiency of 0.018 to 0.02 dB.

4. The bipyramidal device according to claim 1, comprising means (18) for monitoring the physical parameters of the liquid medium within the pyramids (1,2), the means (18) comprising an instrument for measuring specific electrical conductivity of water.

5. The bipyramidal device according to claim 1, wherein the cavity (13) of the lower pyramid (1) is equipped with a leak-proof partition (22), dividing the lower pyramid (1) height-wise at a 1:3 ratio and forming a compartment in a lower part of the lower pyramid (1) for installing the audio-video device (19) and the means (18) for controlling the physical parameters of the liquid medium.

6. The bipyramidal device according to claim 1, comprising a lining material (6) covering triangular walls of the upper pyramid (2) and of the lower pyramid (1), the lining material (6) having a cellular-honeycomb structure (7) and a porosity of 0.75-0.92.

\* \* \* \* \*